(12) United States Patent
Vandenbosch et al.

(10) Patent No.: US 10,283,839 B2
(45) Date of Patent: May 7, 2019

(54) DUAL BAND SRR LOADED CAVITY ANTENNA

(71) Applicant: AGFA NV, Mortsel (BE)

(72) Inventors: Guy Vandenbosch, Mortsel (BE); Ping Jack Soh, Mortsel (BE); Sen Yan, Mortsel (BE); Jan Vercammen, Mortsel (BE)

(73) Assignee: AGFA NV, Mortsel (BE)

( * ) Notice: Subject to any disclaimer, the term of this patent is extended or adjusted under 35 U.S.C. 154(b) by 0 days.

(21) Appl. No.: 15/322,211

(22) PCT Filed: Jul. 2, 2015

(86) PCT No.: PCT/EP2015/065121
§ 371 (c)(1),
(2) Date: Dec. 27, 2016

(87) PCT Pub. No.: WO2016/001370
PCT Pub. Date: Jan. 7, 2016

(65) Prior Publication Data
US 2018/0212308 A1    Jul. 26, 2018

(30) Foreign Application Priority Data
Jul. 3, 2014  (EP) ..................... 14175601

(51) Int. Cl.
*H01Q 1/38*  (2006.01)
*H01Q 1/22*  (2006.01)
*H01Q 5/10*  (2015.01)
*H01Q 5/20*  (2015.01)
*H01Q 9/26*  (2006.01)
*H01Q 13/18* (2006.01)
(Continued)

(52) U.S. Cl.
CPC ........ *H01Q 1/2291* (2013.01); *A61B 6/4283* (2013.01); *A61B 6/566* (2013.01); *H01Q 1/38* (2013.01); *H01Q 5/10* (2015.01); *H01Q 5/20* (2015.01); *H01Q 5/378* (2015.01); *H01Q 9/265* (2013.01); *H01Q 13/18* (2013.01); *H01Q 21/28* (2013.01)

(58) Field of Classification Search
CPC .......... H01Q 1/2266; H01Q 5/10; H01Q 5/20; H01Q 1/2291; H01Q 1/38; H01Q 5/378; H01Q 9/265; H01Q 13/10; H01Q 21/28
See application file for complete search history.

(56) References Cited

U.S. PATENT DOCUMENTS 4,130,823 A * 12/1978 Hoople ................. H01Q 13/18
                                                   343/768
2012/0162015 A1   6/2012  Chen et al.
2013/0010928 A1   1/2013  Hannon et al.

FOREIGN PATENT DOCUMENTS

JP      2003-023315 A    1/2003

OTHER PUBLICATIONS

Official Communication issued in International Patent Application No. PCT/EP2015/065121, dated Sep. 7, 2015.
(Continued)

*Primary Examiner* — Hoang V Nguyen
(74) *Attorney, Agent, or Firm* — Keating & Bennett, LLP

(57) ABSTRACT

A dual band antenna based on open waveguide topology incorporating a radiation slot and integrating a planar resonator for dual band and miniaturization purposes and a cassette for holding a direct radiography sensor provided with at least one such antenna for wireless data transmission.

10 Claims, 4 Drawing Sheets

(51) Int. Cl.
*H01Q 21/28* (2006.01)
*H01Q 5/378* (2015.01)
*A61B 6/00* (2006.01)

(56) References Cited

OTHER PUBLICATIONS

Dong et al., "Promising Future of Metamaterials", IEEE Microwave Magazine, IEEEService Center, vol. 13, No. 2, Mar. 1, 2012, pp. 39-56.

Lin et al., "Design of Dual-Band Millimeter-Wave Antenna-in-Package Using Flip-Chip Assembly", IEEE Transactions on Components, Packaging and Manufacturing Technology, vol. 4, No. 3, Mar. 1, 2014, pp. 385-391.

Weijian et al., "Design of Dual-Polarization Array Antenna Based on Substrate Integrated Waveguide", 2013 IEEE International Conference of IEEE Region 10, Oct. 22, 2013, 4 pages.

* cited by examiner

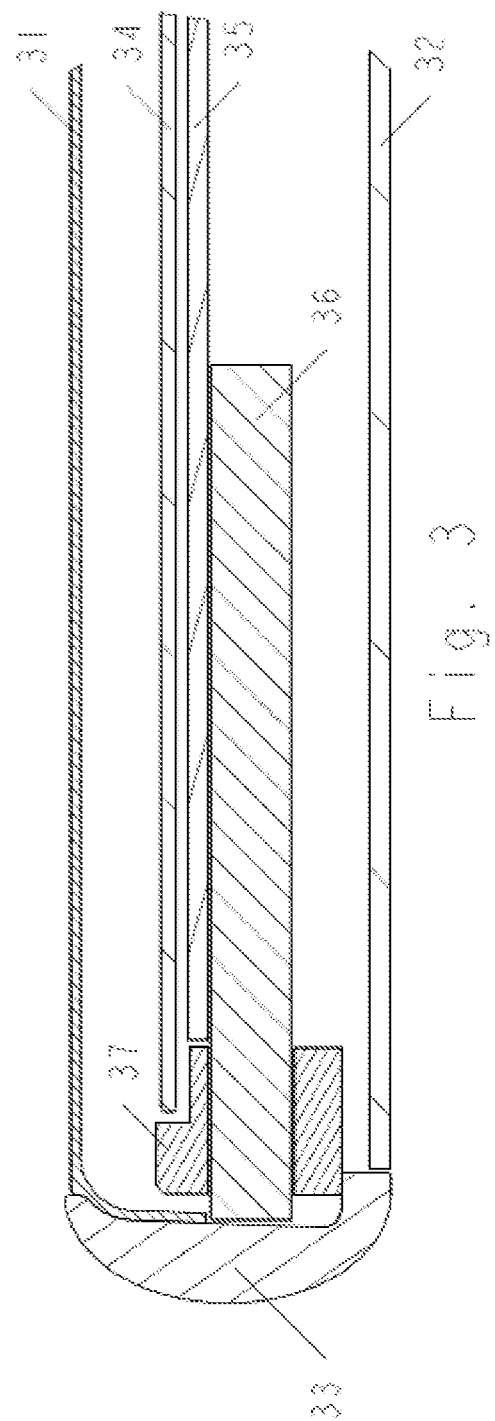

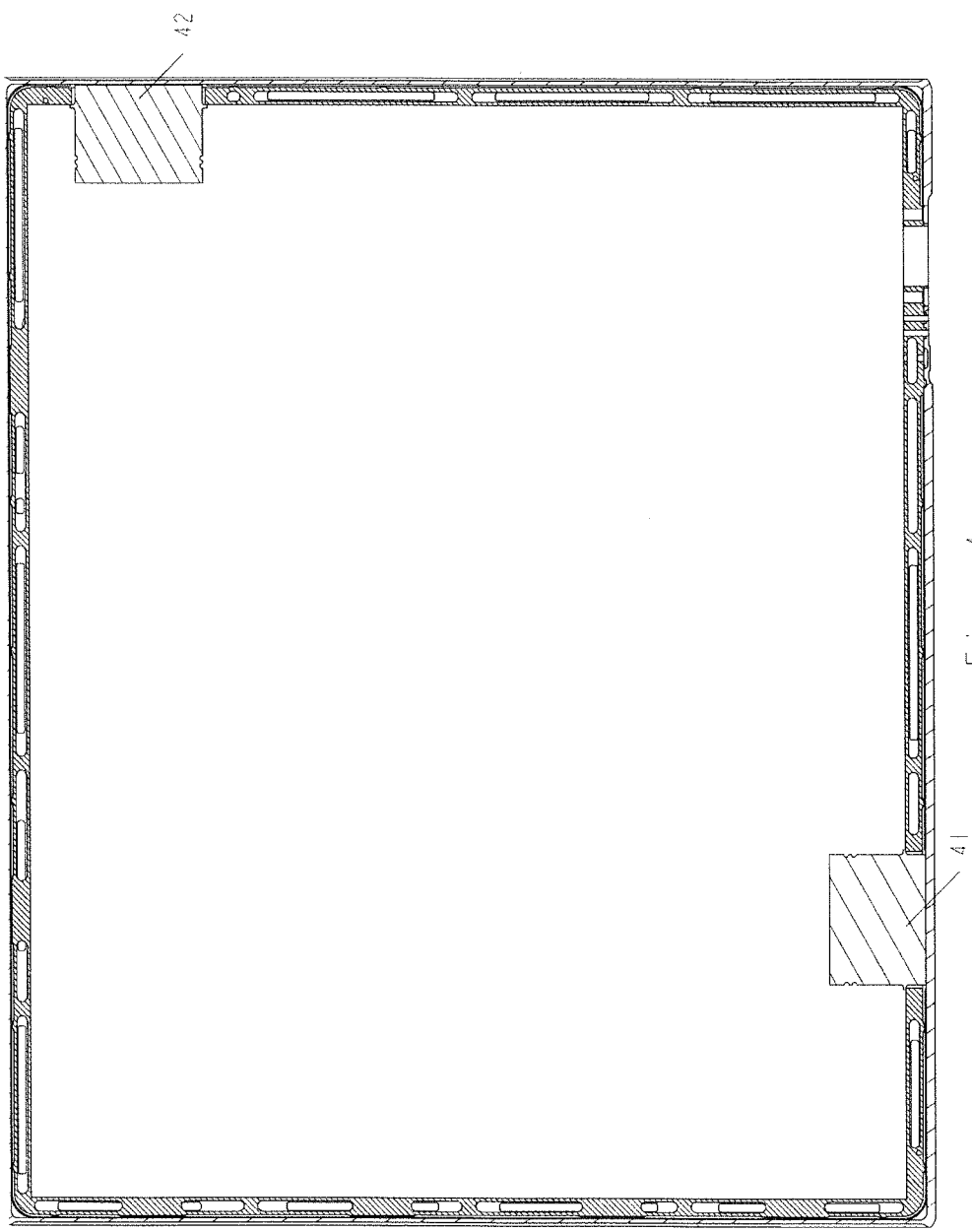

DUAL BAND SRR LOADED CAVITY ANTENNA

CROSS REFERENCE TO RELATED APPLICATIONS

This application is a 371 National Stage Application of PCT/EP2015/065121, filed Jul. 2, 2015. This application claims the benefit of European Application No. 14175601.5, filed Jul. 3, 2014, which is incorporated by reference herein in its entirety.

BACKGROUND OF THE INVENTION

1. Field of the Invention

The present invention relates to an antenna for wireless signal transmission. The invention more particularly relates to such an antenna to be built into a cassette conveying a direct radiography sensor.

2. Description of the Related Art

Direct radiography (DR) is an X-ray imaging technique, wherein a flat panel radiation sensitive detector is used instead of a traditional radiographic film or instead of a radiation sensor comprising a photostimulable phosphor screen (CR technology).

Two different types of such flat panel detectors used for direct radiography exist.

A first group comprises radiation detectors that convert X-rays directly into electric charges. The X-rays interact directly with a photoconductive layer such as amorphous selenium (a-Se) layer.

The second group comprises detectors that have a scintillator layer e.g. consisting of CsI:Tl or Gd2O2S which converts X-rays into light. The light emitted by the scintillator layer then interacts with an amorphous silicon (a-Si) semiconductor layer, where electric charges are created in correspondence with the amount of light detected by the semiconductor layer in each pixel. These electric charges are read out and converted into a digital image representation of the radiation image. This digital image representation can then be applied to a signal processing device and/or to display device and/or can be stored.

Commercial versions of the aforementioned DR detectors are nowadays available in different dimensions and pixel resolutions, depending on the targeted clinical imaging application (such as dental, general radiology, mammography . . . ).

A DR detector comprising the radiation sensor itself and the read-out electronics to read-out the digital image is conventionally conveyed in a cassette.

Care is being taken when designing a DR detector and a cassette for conveying a DR detector to limit size and weight in order to make the use of the assembly convenient. Especially in case of portable detectors, it is important that the cassette incorporating the detector is light weight and thin.

The digital signal representing the radiation image captured by the DR detector is to be communicated from the cassette to an external device where it can be processed and/or displayed and/or stored. Most commonly the signal representation of the radiation image is transmitted to a workstation.

Apart from the data representing the radiation image itself, also other kinds of data may be communicated to and from the cassette such as radiation settings, status information, synchronisation data, all types of identification data such as patient identification data etc.

The data transmission from and to the cassette can be effectuated in a wired or in a wireless way. Both versions are today commercially available.

In case of a wireless version, the cassette comprises an antenna adapted for wireless data transmission in a certain wavelength range.

Such antennas are commercially available. However, as will be described below, the available antennas do not suit the envisaged application.

Because the cassette size, and especially because the thickness of the cassette is optimized for convenient usage, an antenna to be built in such a cassette needs to be miniaturized in order to fit into the available space.

Evidently the antenna's characteristics, more specifically the antenna's dimensions and topology must further be adapted to the applicable wavelengths for the envisaged transmission. In the present application WIFI data transmission is envisaged. The carrier frequencies in two WIFI bands according to the IEEE802.11 standard are the 2.4 GHz and the 5.8 GHz WLAN bands (although the actual bandwidth applicable for WIFI transmission extends beyond these specific frequencies).

Commercially available antennas have a drawback that due to their dimensions they can only be built into the cassette in such a way that they emit radiation in a direction in which the cassette attenuates signal transmission due to radiation absorbing characteristics of sensor or cassette components. For example a radiation absorbing layer such as a back scatter absorbing layer (e.g. implemented as a lead layer or an additional scintillator layer) might cause signal attenuation.

Furthermore, when the cassette is placed in a bucky device at x-ray image recording, the components of the bucky device itself may cause attenuation of the signal transmission.

It is evident that such signal attenuation is to be avoided.

SUMMARY OF THE INVENTION

Preferred embodiments of the present invention provide a dual band antenna which emits at the envisaged wavelengths for WIFI transmission and that has a topology that is optimal for building it into a DR cassette.

The above is realised by an antenna having the topology set out below.

Specific features for preferred embodiments of the invention are also set out below.

The design of the antenna according to a preferred embodiment of the present invention is based on open waveguide technology.

The antenna is formed in a solid state cavity formed as a printed circuit board, thereby using a metallic and dielectric stable high-frequency laminate.

One example of such a laminate is a Rogers RO4003 material.

The antenna comprises a waveguide resonator formed within the substrate area, the antenna dimensions being adapted for signal transmission within the dual bandwidth ranges prescribed for WIFI transmission in the IEEE 802.11 standard.

A number of juxtaposed vias are used to form the waveguide resonator's metallic walls. An opening in between the juxtaposed vias serves as a radiation slot.

An additional planar resonator is integrated into the above described resonator to enable signal transmission (in an additional bandwidth range) within the dual bandwidth ranges prescribed for WIFI transmission in the IEEE 802.11 standard. This additional resonator preferably has the form of a split ring resonator (SRR). A rectangular shaped split ring resonator is a suitable embodiment of such a split ring resonator. Other types and forms of planar resonators are possible.

The dimensions and geometry of the antenna components is tuned to obtain antenna operation in the bandwidth ranges prescribed by the IEEE 802.11 standard for wireless transmission.

The structure is fed by a signal feeder, for example, a stripline (50Ω) and a feeding probe coupled to the stripline and feeding the signal to the strip line.

In one embodiment vias are also provided on both sides of this strip line at about λ/4 (calculated using the guided wavelength at 2.45 GHz) in order to avoid parallel plate modes.

In a specific embodiment vias are spaced at 1.5 mm throughout the complete design so as to form the metallic walls of the cavity.

Preferred embodiments of the invention further provide a cassette conveying a direct radiography detector and having at least one antenna as described above.

The antenna is preferably positioned so it emits radiation in a direction where radiation transmission is not attenuated by radiation absorbing components part of the cassette or the DR detector assembly.

Further details on the cassette are set out below.

Further advantages and embodiments of the present invention will become apparent from the following description and drawings.

BRIEF DESCRIPTION OF THE DRAWINGS

FIG. 3 is a cross section of a DR cassette incorporating an antenna according to a preferred embodiment of the present invention.

FIG. 4 schematically shows the location of two antennas according to a preferred embodiment of the present invention in a DR cassette as shown in FIG. 3.

DETAILED DESCRIPTION OF THE PREFERRED EMBODIMENTS

Figure 1:
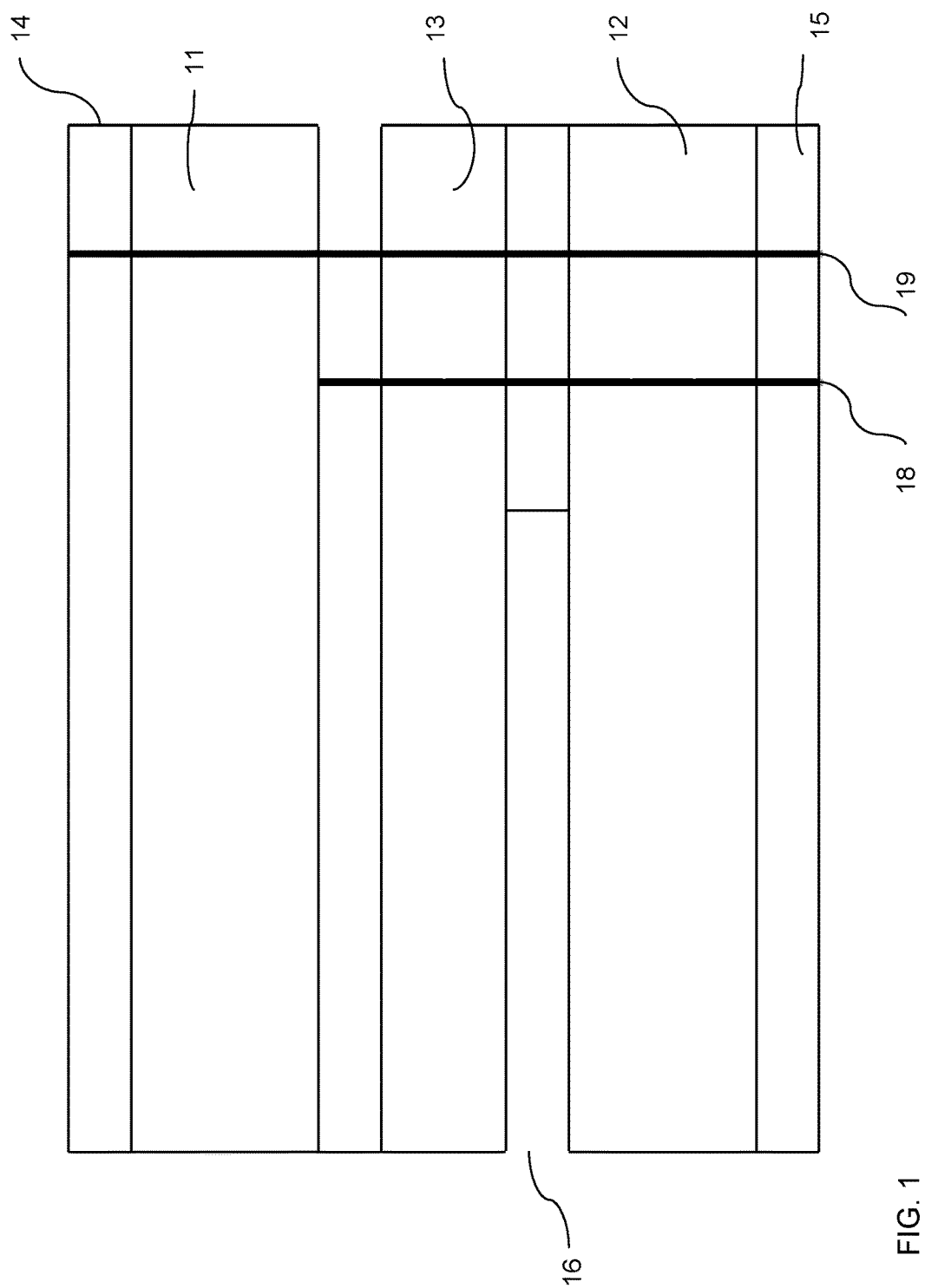
FIG. 1 is a cross section showing the different layers of the composition of an antenna according to a preferred embodiment of the present invention.

The antenna according to a preferred embodiment of the present invention has a printed circuit board composition as shown in FIG. 1. It comprises a mechanical and dielectric stable high-frequency laminate.

In a specific embodiment two layers (11, 12) of such mechanical and dielectric stable high-frequency material, more specifically of Rogers RO4003C material (thickness 1.5424 mm, permittivity 3.38, and loss tangent 0.0021) are bonded by a bonding layer (13) of IS400 high performance pre-impregnated fibres (prepreg) (0.46 mm thick, permittivity 3.9, loss tangent 0.022) and form a substrate. Both layers (11, 12) of the dielectric stable material are covered on the outside face with a conductive layer such as copper layer (14, 15).

In the above-described substrate a cavity is formed by a number of juxtaposed vias (19).

A planar resonator, in this embodiment implemented as a rectangular shaped split ring resonator (16) is provided in between the prepreg layer and one of the layers of Rogers material.

A 50Ω strip line (17) and a feeding probe (18) are provided for feeding the structure is provided in between one layer (11) of dielectric material and prepreg layer (13).

Figure 2:
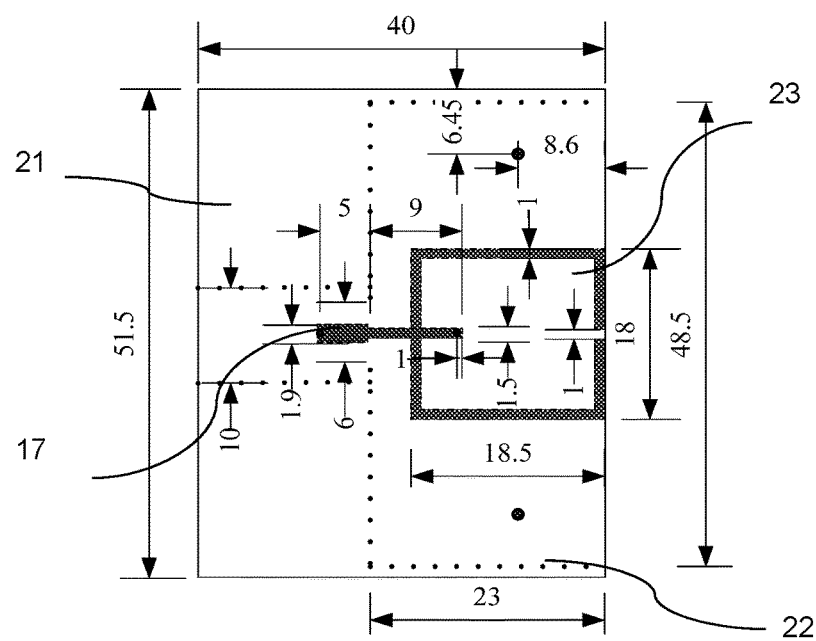
FIG. 2 is a top view of an antenna according to a preferred embodiment of the present invention wherein the antenna's dimensions are shown (dimensions in mm).

FIG. 2 shows a cavity (21), sized at 23×48.5 mm$^2$ and embedded within dielectric layers (11,12) and copper layers (14,15).

Vias (22) having a diameter of 0.45 mm are used to form the metallic walls of the cavity. One of the 48.5 mm sides of the cavity is partially left open (no vias provided) in order to function as a radiating slot.

A rectangular shaped split ring resonator SRR (23) (sized at 18×18.5 mm$^2$) is integrated into the cavity to enable additional bandwidth in the 2.45 GHz band.

The structure is fed by a 50Ω stripline (17) provided in between the layer of Rogers material and prepreg layer.

Additional vias sized at 0.45 mm in diameter are implemented on both sides of this stripline at about λ/4 (calculated using the guided wavelength at 2.45 GHz) in order to avoid parallel plate modes. The vias are spaced at about 1.5 mm throughout the complete design.

The antenna was designed to be built into a cassette conveying a direct radiography detector.

A cross sectional view of part of such a cassette is shown in FIG. 3. The cassette comprises a housing composed of a top cover (31) and a bottom plate (32) and side walls (33) connecting top cover layer (33) with the bottom plate (32). In the illustrated embodiment a shock absorber (33) at least partially covers the side walls to prevent the cassette from being damaged during handling. Holders (37) are provided to secure the different components in the cassette. The cassette forms a fully covered metallic enclosure.

FIG. 3 further shows the radiography detector (34) conveyed in the cassette. The detector basically comprises a radiation sensitive part and read-out electronics. Additional layers such as a back-scatter preventing layer can be provided. Back scatter prevention can be obtained e.g. by an additional scintillator layer. FIG. 3 also shows the detector's carbon base plate (35). Under the carbon base plate (between base plate and bottom plate) an antenna (36) is located.

Preferably the antenna is positioned so that it emits the signal to be transmitted into a direction in which no signal attenuating components of the DR detector or cassette components are present or at least into a direction in which signal attenuation is low (more particularly in a direction in which signal attenuation is equal to or lower than in other directions).

In a specific embodiment this goal is achieved by positioning the antenna in such a way that its radiation slot faces one of the side walls of the cassette.

The cassette may comprise more than one antenna according to this invention. Embodiments having more than one such antennas are advantages in that attenuation of the signal emitted by one antenna by components external to the cassette, e.g. by parts of a bucky device used when recording the x-ray image, can be avoided by picking up the signal emitted by another antenna the operation of which is not hindered by the external component.

In one embodiment two antennas are provided positioned in a way as will be described below so as to see that independently of the manner in which the cassette is placed during irradiation, there is always a radiation slot of one of the antennas provided in the cassette that is optimally positioned for signal transmission.

It will be clear that the invention is not limited to the use of two antennas. Embodiments with more antennas are also possible.

FIG. 4 shows a top view of the bottom plate of an embodiment of a DR cassette comprising two antennas according to the present invention. The bottom plate has a rectangular form. Two antennas (41, 42) are provided on the bottom plate of the cassette, one (41) having its radiation slot facing one of the short side walls of the cassette, the other one (42) being placed so that its radiation slot faces the one of the long side walls of the cassette.

Irrespective of the positioning of the cassette in the radiation image acquisition system, one of the antennas will be optimally positioned for signal transmission.

The invention claimed is:

1. A dual band cavity antenna comprising:
a substrate having a substantially constant dielectric value;
a waveguide resonator embedded within the substrate, the waveguide resonator including an upper conductive layer and a lower conductive layer covering the substrate, and metallic walls connecting the upper conductive layer with the lower conductive layer to define a cavity therein, the metallic walls including juxtaposed vias and including a radiation slot defined by an opening between the juxtaposed vias;
a planar resonator integrated in the waveguide resonator; and
a signal feeder that feeds signals into the planar resonator; wherein
the dual band cavity antenna has dimensions that transmit WIFI signals according to IEEE 802.11 standard.

2. The dual band cavity antenna according to claim 1, wherein the planar resonator is a split ring resonator.

3. The dual band cavity antenna according to claim 1, wherein the signal feeder includes a stripline and a feeding probe.

4. The dual band cavity antenna according to claim 3, further comprising additional vias provided on both sides of the stripline.

5. A cassette for housing an X-ray detector, the cassette comprising:
at least one dual band cavity antenna according to claim 1.

6. The cassette according to claim 5, wherein the at least one dual band cavity antenna is positioned in the cassette so as to emit signals in a direction having low signal attenuation by components of the cassette or the X-ray detector.

7. The cassette according to claim 6, further comprising an upper layer, a bottom layer, and side walls joining the upper layer with the bottom layer; wherein
the at least one dual band cavity antenna is positioned so that it emits signals in a direction of one of the side walls.

8. The cassette according to claim 7, wherein the radiation slot faces the one of the side walls.

9. The cassette according to claim 5, further comprising another dual band cavity antenna.

10. The dual band cavity antenna according to claim 1, wherein each of the waveguide resonator and the planar resonator emit signals from a side of the cavity.

* * * * *